United States Patent
Collura

(10) Patent No.: US 6,931,275 B2
(45) Date of Patent: Aug. 16, 2005

(54) SYSTEM FOR REDUCTION OF UNDESIRABLE BRAIN WAVE PATTERNS USING SELECTIVE PHOTIC STIMULATION

(76) Inventor: Thomas F. Collura, P.O. Box 24450, Mayfield Heights, OH (US) 44124

( * ) Notice: Subject to any disclaimer, the term of this patent is extended or adjusted under 35 U.S.C. 154(b) by 186 days.

(21) Appl. No.: 10/164,543

(22) Filed: Jun. 7, 2002

(65) Prior Publication Data

US 2003/0229291 A1 Dec. 11, 2003

(51) Int. Cl.[7] ................................................ A61B 5/04
(52) U.S. Cl. ................................................... 600/545
(58) Field of Search ................... 600/545, 27, 544, 600/558; 434/236, 238; 463/36, 37, 38

(56) References Cited

U.S. PATENT DOCUMENTS

| | | | |
|---|---|---|---|
| 5,331,969 A | * | 7/1994 | Silberstein .................. 600/544 |
| 5,495,853 A | * | 3/1996 | Yasushi ...................... 600/545 |
| 5,546,943 A | | 8/1996 | Gould |
| 5,899,867 A | * | 5/1999 | Collura ....................... 600/545 |
| 6,450,820 B1 | * | 9/2002 | Palsson et al. .............. 434/236 |

* cited by examiner

*Primary Examiner*—Max F. Hindenburg
*Assistant Examiner*—Brian Szmal
(74) *Attorney, Agent, or Firm*—Roetzel & Andress

(57) ABSTRACT

A method of reducing undesirable brain wave pattern using selective photic stimulation. Electrodes, attached to a subject's scalp, transmit electroencephalographic (EEG) signals from the subject. These signals are in response to the photic stimulation being displayed to the subject. The resultant EEG signals are then filtered, while control logic monitors a predetermined EEG frequency band and feeds back the filtered EEG signal to the subject via the photic stimulation. The photic stimulator is then turned on and off rapidly, in response to the amount of energy in a predetermined band of the subject's EEG, with the intent of reducing an undesirable brain rhythm.

6 Claims, 2 Drawing Sheets

SYSTEM FOR REDUCTION OF UNDESIRABLE BRAIN WAVE PATTERNS USING SELECTIVE PHOTIC STIMULATION

FIELD OF THE INVENTION

The present invention relates generally to a method for stimulating dynamic sensory brain processes, and more particularly, to a method for reducing undesirable brain wave processes using selective, repetitive photic stimulation.

BACKGROUND OF THE INVENTION

The origin and nature of brain waves as measured from the human scalp has been a topic of ongoing research. For example, the electroencephalogram (EEG) as measured from the intact human scalp is of interest in psychology and psychophysics because it can provide an indication of the activity of brain cells in the awake, alert state. Of particular use are the minute potentials evoked by sensory stimuli, for these time-locked transient wavelets show how populations of cells behave in response to afferent volleys carried by primary sensory fibers.

Whenever a brief stimulus is presented to a trainee, there is a transient brain response due to that stimulation. The signal produced in the EEG is generally very small, but it can be detected. In cases where it is possible to discern the EEG changes, either in the raw EEG or in a processed form, then there is said to be an event-related potential (ERP), particularly a sensory evoked potential. The evoked potential provides an indication of the effect of the stimulus on the brain, and it has been established that the EP is sensitive to changes in sensory and perceptual processes.

When muscle and eye movements are minimized by relaxation, the predominant sources of scalp potential are these populations of cells in the brain, with large cortical cells providing the majority of the voltage. Due to the distribution of ions across active membranes, each cell tends to take on dipole characteristics and produce potentials which are carried to the scalp by volume conduction. When cells polarize in asynchrony, the net surface potential is small due to the cancellation of out-of-phase components. The presence of a measurable surface potential thus depends on the fact that some cells are polarizing in synchrony, generally in response to an afferent volley in which fibers are firing in unison.

The brain produces a multitude of frequencies that can be measured in the EEG. These can be broken into commonly recognized bands, including alpha (8–12), beta (12–20), and theta (4–7). It is found that the relative preponderance of these rhythms is a valuable indicator of global brain state, as well as short-term variations in brain state. In certain cases, it is possible to identify desirable as well as undesirable states, on the basis of the relative amounts of these rhythms. In particular, an excessive amount of theta waves is associated with a dreamlike, distracted, or inattentive state. In cases where it is desired to discourage these states, it is beneficial to have methods that encourage the brain to reduce the amount of these waves, on both a short-term basis, and in the long-term, as a method of training the brain to naturally reach more desirable states.

It has also been observed that sensory stimulation has specific effects on the EEG. These include both evoked potentials (signals that are introduced into the EEG due to the stimulation) and extinction phenomena (signals that are removed from the EEG due to the stimulation). In particular, the theta wave can be reduced by a stimulus that produces an alerting or re-orienting response. Such a stimulus has the effect of startling or alerting the brain, and can be presented in such a manner that endogenous rhythms (including theta and alpha) are extinguished, at least temporarily, by the presentation of the stimulation.

When such stimulation is provided in a contingent manner (depending on the details of the EEG at some time), then there is an opportunity for the brain to learn, either by classical conditioning, or by operant conditioning. It is thus desirable to develop methods that allow the selective presentation of specific stimuli, based upon parameters derived from the EEG. Such methods can provide nonvolitional feedback methods, that do not depend on the intentions or understanding of the trainee, thus providing robust and immediate mechanisms for brain modification.

At this time, the use of contingent stimulation in the context of EEG biofeedback ("neurofeedback") is not a well developed field. In particular, there are no well-defined methods that use EEG parameters for the presentation of specifically activating (or de-activating) stimuli, in the context of brain modification via the EEG.

SUMMARY OF THE PRESENT INVENTION

The present invention overcomes these and other deficiencies of the prior art, by providing a method of reducing undesirable brain wave patterns using selective photic stimulation. The invention is based on selectively introducing light stimulation at a predetermined rate, and at selected moments in time when the undesirable brain rhythm is found to be present. The method is based upon the fact that the photic stimulation, which is only provided at precise moments when the undesirable rhythm is present, creates a conditioning effect on the brain which will selectively reduce that undesirable rhythm. The method is especially advantageous in that it requires no instructions or intention on the part of the subject, and provides immediate and direct results.

In accordance with one general aspect of the invention, there is provided a method of reducing undesirable brain wave patterns using selective photic stimulation. Electrodes are placed on a subject's scalp. Then photic stimulation is displayed to the subject. Generally, the photic stimulation is presented as a display lamp fitted with LED's and positioned in front of the subject. The electrodes then transmit an electroencephalographic (EEG) signal from the subject while the stimuli is being displayed. The resultant EEG signal is then sent to a filter and filtered. Control logic then monitors a predetermined EEG frequency band and feeds back the filtered EEG signal to the subject via the photic stimulation. The photic stimulator is then turned on and off rapidly, in response to the amount of energy in a predetermined band of the subject's EEG. The photic stimulator is then activated at specific times, with the intent of reducing an undesirable brain rhythm in a subject's EEG.

In a particular embodiment of the invention, there is provided a method of monitoring short-term changes in a subject's brain state. The method is basically the same as above, except that a predetermined EEG frequency band is not monitored. Instead, short-term changes in a subject's EEG rhythms are recorded and then used to control the photic stimulator. Thus, the method focuses only on monitoring short-term changes in the subject's brain state.

These and other aspects of the present invention are herein described in further detail, with reference to the accompanying Figures, the illustrated embodiments being representative of only some of the ways in which the principles and concepts of the invention can be executed and employed.

DETAILED DESCRIPTION OF PREFERRED AND ALTERNATE EMBODIMENTS

The present invention provides a method for reducing brainwave patterns that are deemed undesirable, and for which it is desired to reduce their prevalence or amplitude in the EEG (electroencephalogram). It is based on selectively introducing light stimulation at a predetermined rate (flashes per second), and at selected moments in time when the undesirable brain rhythm is found to be present, based on real-time measurement and processing of the EEG. Because the photic stimulation is provided only at the precise moments when the undesirable rhythm is present, there is a conditioning effect on the brain, which will selectively reduce that rhythm. This reduction will be seen in the EEG. Thus, the presentation of specific stimuli can be used to train the brain to produce specific brain wave processes, which in turn allows the brain to naturally reach more desirable states.

Figure 1:
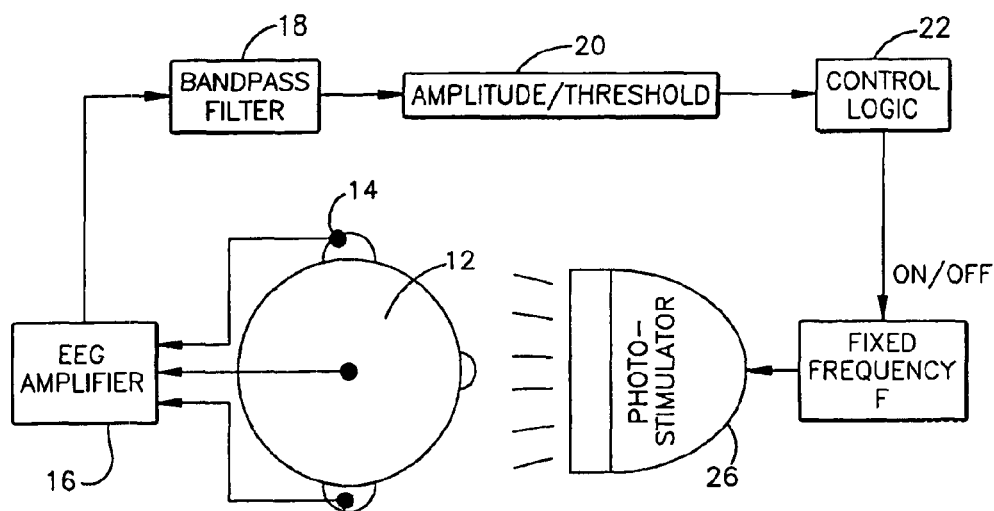
FIG. 1 is a schematic view of the basic system for reduction of undesirable brain patterns using selective photic stimulation.

Referring to FIG. 1, the procedure is as follows. Electrodes 14 secured to the subject's head 12, transmit EEG signals produced by photic stimulation 26 to the EEG amplifier 16. These signals are then fed into bandpass (digital) filters 18, which filter the signals at predetermined EEG frequencies to filter out unwanted signals. These EEG signals are then monitored for a baseline period, to determine the natural level of the relevant brain rhythms. Amplitude determination logic inputs the signals and determines an appropriate threshold 20 for activation of the photic stimulation 26. Typically, this is based on an amplitude criterion, triggered by the output of the digital filters 18 or the FFT (fast fourier transform) processing.

Visual stimuli 26 presented to the subject 12, is controlled by the control logic system 22. The control logic system 22 contains a digitizer, which along with the controller, allows for the selecting of the intensity of stimulation, frequency of stimulation, and/or time of stimulation. Photic stimulation 26 can be introduced to the subject 12 in a variety of ways. Glasses fitted with LED's or similarly fast-responding light sources can be worn by the subject 12. A display lamp fitted with LED's or similarly fast-responding light sources can be positioned directly in front of the subject 12. Or, a computer display with selectively activated components can be displayed to the subject 12. The photic stimulation 26 may be a continuous light, or a repetitive light, as well.

Finally, a computer processor uses a computer algorithm to measure and reconstruct the EEG signal. The algorithm also has the ability to control the filters 18 which filter out selected components of the EEG signal based upon specific frequency characteristics.

In operation, an EEG frequency is selected to stimulate or reduce. The EEG frequency which is to be stimulated is selected based upon it being sufficiently rapid to alert the brain to the stimulation. Whereas, the frequency which is to be reduced, for example 4–7 Hz, is deemed the "inhibit band". Then a threshold 20 is set for control of the photic stimulation 26. The photic stimulation 26 is then turned on at a selected frequency based upon the EEG having energy exceeding threshold 20 for the inhibit band. The photic stimulation 26 is then enabled, based upon the control logic 22. The photic stimulation 26 is then administered selectively for a short period of time (1–10 minutes). The stimulation 26 is then discontinued and the feedback is recorded. For example, if 12 flash per second stimulation is delivered whenever the subject's theta wave (4–7 Hz) exceeds a threshold value 20, the system has an effect of extinguishing excessive EEG theta by the simple mechanism of distracting and engaging the cortex, so that theta cannot be produced at such a large level.

Figure 2:
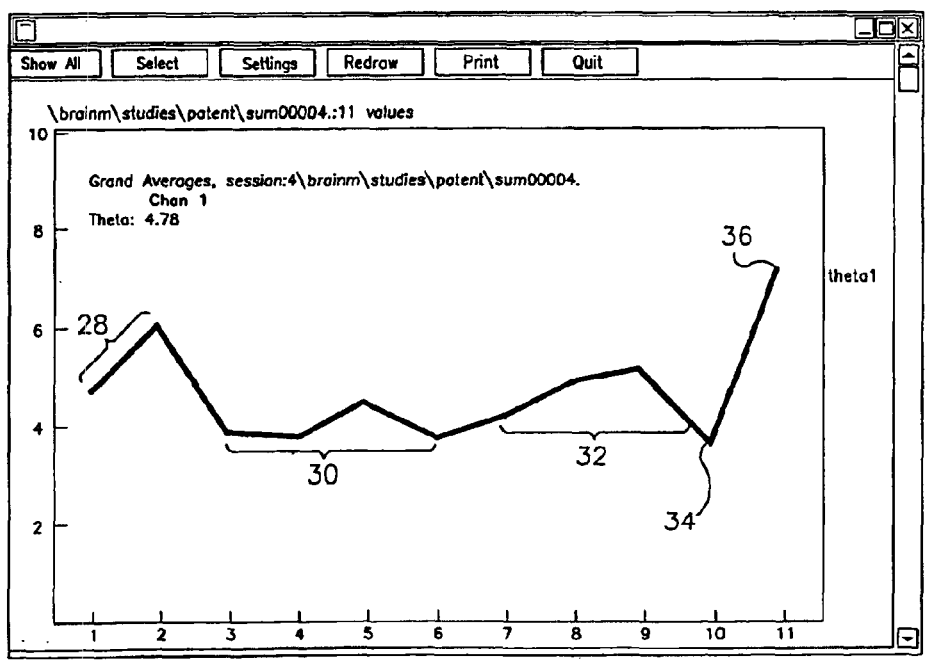
FIG. 2 is a graph showing the response of the EEG theta wave during selective photic stimulation.

Referring to FIG. 2, demonstration of the reduction of EEG by virtue of the introduction of selective visual stimulation is shown. The first two minutes depict baseline levels with no feedback 28. The next four minutes illustrate "suppression" activity when feedback is provided 30. The EEG responses show reduced theta levels below any baseline level. The next three minutes illustrate "recovery" of the theta 32. Feedback is withdrawn allowing the theta wave to rise again toward baseline levels. The next minute illustrates the EEG response as suppression is re-introduced 34. Feedback is provided causing the theta wave to reduce again below the baseline levels. The final minute is illustrative of the EEG post suppression response 36. Feedback is withdrawn causing the theta wave to rise again to reach and exceed baseline levels.

Figure 3:
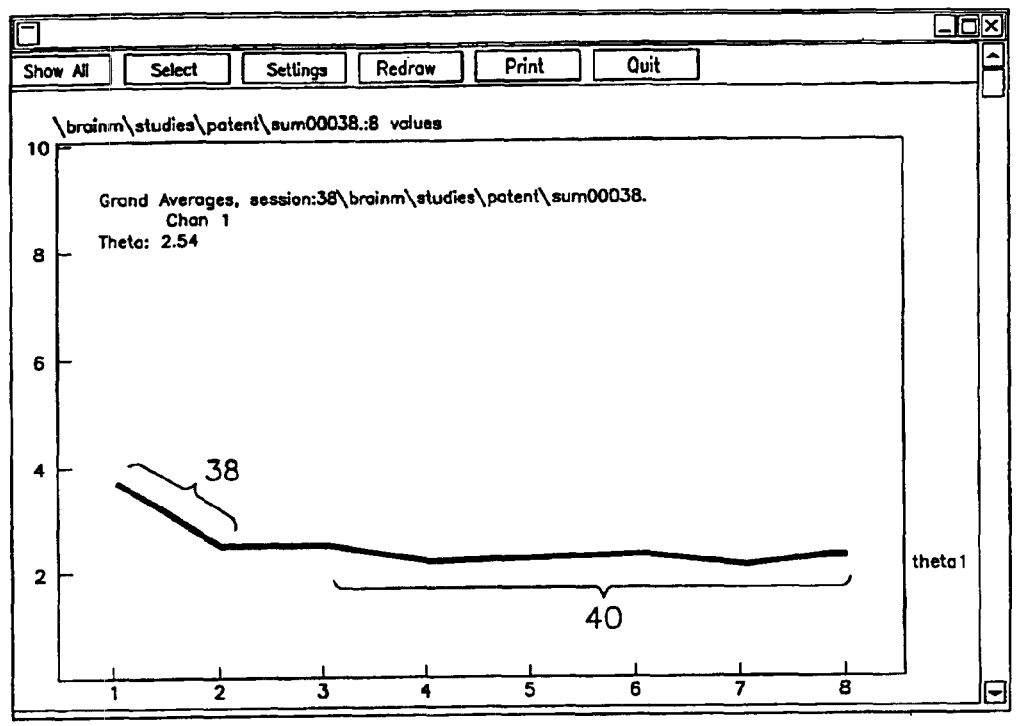
FIG. 3 is a graph showing the response of the EEG theta wave during selective photic stimulation.

The second demonstration shows similar reduction of theta, see FIG. 3. The first two minutes illustrate baseline levels with no feedback 38. The next six minutes illustrate suppression of the theta wave 40. Feedback is provided causing the theta wave to be held down to levels below the baseline level.

Figure 4:
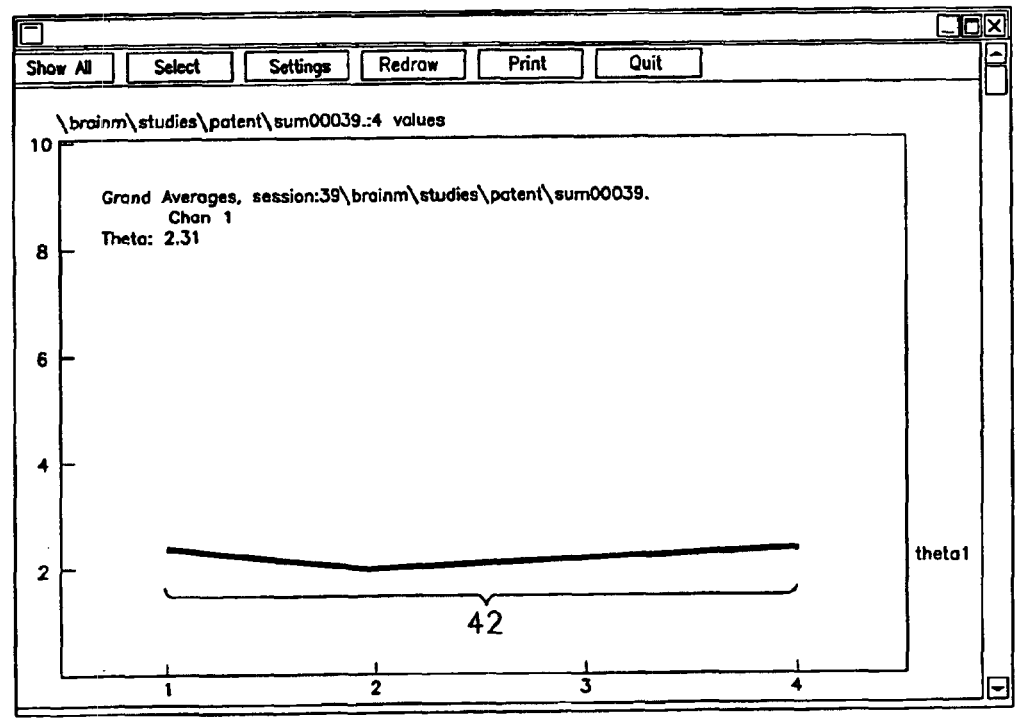
FIG. 4 is a graph showing the response of the EEG theta wave during subsequent conventional neurofeedback.

Referring to FIG. 4, a similar reduction of theta is shown, but it is followed by a neurofeedback training session. For four minutes, the theta level is being held down by conventional neurofeedback 42, after the above method of reducing theta was introduced. It shows that the reduction of theta is maintained, and held down, by neurofeedback training. This illustrates that this technique is valuable as a precursor or "training wheels" for conventional neurofeedback training (operant conditioning).

When this method is used, it is not necessary to give instructions to the subject. This method is not a case of conventional, "volitional" neurofeedback. It is an example of "nonvolitional" neurofeedback, in which the neurofeedback signal has an intrinsic effect on the subject's brain. The learning process is one of classical conditioning, not one of operant conditioning. The advantage of this method is that it requires no instructions or intention on the part of the subject, and provides immediate and direct results. As a precursor to volitional neurofeedback, it makes it possible to prime the brain to be in a desired state, and to be better responsive to the conventional feedback signals, when they are presented.

When we combine volitional and non-volitional neurofeedback, we may be able to produce a more rapid initial ramp-up to the learning process. We can provide an ongoing assist ("training wheels"), or we can assist with difficult aspects, for example, a subject having difficulty with theta reduction. This can provide more aggressive reduction of undesirable rhythms, can introduce the brain to particular states, and may combine such effects, in a single neurofeedback protocol.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

What is claimed as the invention is:

1. A method of reducing undesirable brain wave patterns using selective photic stimulation, comprising the steps of:
   securing electrodes to a subject's scalp;
   displaying stimuli to the subject;
   receiving an electroencephalographic (EEG) signal from the subject while the stimuli is being displayed;
   transmitting the resultant EEG signal to a filter;
   filtering the EEG signal;
   monitoring a predetermined EEG frequency band;
   and feeding back the filtered EEG signal to the subject via photic stimulation, by controlling the presence or absence of the photic stimulation;
   wherein a fixed photic stimulation frequency is employed, regardless of the frequency content of a trainee's EEG rhythms.

2. A method of reducing undesirable brain wave patterns using selective photic stimulation, comprising the steps of:
   securing electrodes to a subject's scalp;
   displaying stimuli to the subject;
   receiving an electroencephalagraphic (EEG) signal from the subject while the stimuli is being displayed;
   transmitting the resultant EEG signal to a filter;
   filtering the EEG signal;
   monitoring a predetermined EEG frequency band;
   and feeding back the filtered EEG signal to the subject via photic stimulation, by controlling the presence or absence of the photic stimulation;
   wherein the photic stimulation is presented by a photic stimulator, which is a display lamp fitted with LED's positioned in front of the subject;
   wherein a photic stimulator is turned on and off rapidly, in response to the amount of energy in a predetermined frequency band of a subject's EEG;
   wherein the photic stimulator is activated at specific times, with the intent of reducing the amount of an undesirable brain rhythm in a subject's EEG;
   wherein the process is used for brief times, such as 1 to 10 minutes, preferably as a precursor to conventional EEG neurofeedback training, as an assist to the neurofeedback training to cause the brain rhythm to reduce the amount of an undesirable rhythm;
   wherein the process employs classical conditioning instead of operant conditioning, so that learning takes place without instructions to the subject, and independent of the subject's intention to undertake training;
   wherein the process employs non-volitional feedback, so that the effect on the subject's EEG does not depend on instructions to the subject, or the subject's intent to undertake training.

3. A method of reducing undesirable brain wave patterns using selective magnetic, tactile or other stimulation, comprising the steps of:
   securing electrodes to a subject's scalp;
   displaying stimuli to the subject;
   receiving an electroencephalographic (EEG) signal from the subject while the stimuli is being displayed;
   transmitting the resultant EEG signal to a filter;
   filtering the EEG signal;
   monitoring a predetermined EEG frequency band;
   and feeding back the filtered EEG signal to the subject via stimulation, by controlling the presence or absence of stimulation;
   wherein the stimulation is turned on and off rapidly, in response to the amount of energy in a predetermined frequency band of a subject's EEG;
   wherein the stimulation is activated at specific times, with the intent of reducing the amount of an undesirable brain rhythm in a subject's EEG;
   wherein the process is used for brief times, such as 1 to 10 minutes, preferably as a precursor to conventional EEG neurofeedback training, as an assist to the neurofeedback training to cause the brain rhythm to reduce the amount of an undesirable rhythm;
   wherein the process employs classical conditioning instead of operant conditioning, so that learning takes place without instructions to the subject, and independent of the subject's intention to undertake training;
   wherein the process employs non-volitional feedback, so that the effect on the subject's EEG does not depend on instructions to the subject, or the subject's intent to undertake training,
   and wherein the stimulation reduces the amount of energy in a particular band in a subject's EEG, via classical conditioning.

4. A method of reducing undesirable brain wave patterns using selective photic stimulation, comprising the steps of:
   securing electrodes to a subject's scalp; displaying stimuli to the subject; receiving an electroencephalographic (EEG) signal from the subject while the stimuli is being displayed;
   transmitting the resultant EEG signal to a filter; filtering the EEG signal;
   monitoring a predetermined EEG frequency band; and feeding back the
   filtered EEG signal to the subject via photic stimulation, by controlling the presence or absence of the photic stimulation,
   wherein a fixed photic stimulation frequency is employed, regardless of the frequency content of a trainee's EEG rhythms.

5. A method of reducing undesirable brain wave patterns using selective photic stimulation, comprising the steps of:
   securing electrodes to a subject's scalp;
   displaying stimuli to the subject;
   receiving an electroencephalographic (EEG) signal from the subject while the stimuli is being displayed;
   transmitting the resultant EEG signal to a filter;
   filtering the EEG signal;
   monitoring a predetermined EEG frequency band; and
   feeding back the filtered EEG signal to the subject via photic stimulation, by controlling the presence or absence of the photic stimulation;

wherein the photic stimulation is presented by a photic stimulator, which is a display lamp fitted with LED's positioned in front of the subject;

wherein the photic stimulator is turned on an off rapidly, in response to the amount of energy in a predetermined frequency band of a subject's EEG, the photic stimulator is activated at specific times, with the intent of reducing the amount of an undesirable brain rhythm in a subject's EEG;

wherein the process is used for brief times, such as 1 to 10 minutes, preferably as a precursor to conventional EEG neurofeedback training, as an assist to the neurofeedback training to cause the brain rhythm to reduce the amount of an undesirable rhythm;

wherein the process employs non-volitional feedback, so that the effect on the subject's EEG does not depend on instructions to the subject, or the subject's intent to undertake training.

6. The method of claim 5 wherein the photic stimulator may be replaced with a magnetic, tactile, or other stimulator, to reduce the amount of energy in a particular band in a subject's EEG, via classical conditioning.

* * * * *